United States Patent [19]

Mushabac

[11] Patent Number: 5,448,472
[45] Date of Patent: Sep. 5, 1995

[54] METHOD USING REFERENCE INDICIA ON TAPE ATTACHED TO MOUTH SURFACE TO OBTAIN THREE DIMENSIONAL CONTOUR DATA

[76] Inventor: David R. Mushabac, 919 Ocean Ave., Brooklyn, N.Y. 11226

[21] Appl. No.: 613,354

[22] Filed: Nov. 14, 1990

Related U.S. Application Data

[63] Continuation-in-part of Ser. No. 507,162, Apr. 10, 1990.

[51] Int. Cl.⁶ .............................................. G06F 15/42
[52] U.S. Cl. .......................... 364/413.28; 364/474.37
[58] Field of Search ................ 128/660; 364/413.28, 364/474.03, 474.05, 474.24, 474.37

[56] References Cited

U.S. PATENT DOCUMENTS

| | | |
|---|---|---|
| 3,971,133 | 7/1976 | Mushabac . |
| 4,182,312 | 1/1980 | Mushabac . |
| 4,239,431 | 12/1980 | Davini . |
| 4,349,277 | 9/1982 | Mundy et al. . |
| 4,431,420 | 2/1984 | Adair . |
| 4,436,684 | 3/1984 | White . |
| 4,525,858 | 6/1985 | Cline et al. . |
| 4,564,295 | 1/1986 | Halioua . |
| 4,569,358 | 2/1986 | Gormley . |
| 4,575,805 | 3/1986 | Moermann et al. . |
| 4,577,968 | 3/1986 | Makosch . |
| 4,611,288 | 9/1986 | Duret et al. . |
| 4,657,394 | 4/1987 | Halioua . |
| 4,663,720 | 5/1987 | Duret et al. . |
| 4,705,037 | 11/1987 | Peyman et al. . |
| 4,763,791 | 8/1988 | Halverson et al. . |
| 4,791,060 | 12/1988 | Schneider et al. ............... 128/653.1 |
| 4,837,732 | 6/1989 | Brandestini et al. . |
| 4,885,844 | 12/1989 | Chun . |
| 4,936,862 | 6/1990 | Walker et al. . |
| 4,941,826 | 7/1990 | Loran et al. . |

OTHER PUBLICATIONS

"Optical Methods to Measure Shape and Size," P. M. Boone *Adv. Dent. Res.* 1(1):27–38, Oct., 1987.
"Optical Method to Measure Shape and Size," P. M. Boone (paper).

*Primary Examiner*—Robert A. Weinhardt
*Attorney, Agent, or Firm*—R. Neil Sudol; Henry D. Coleman

[57] ABSTRACT

In a method for collecting via a video camera three-dimensional surface information in dental applications, a tape strip is applied to a tooth surface to provide a distance reference or standard for use by a computer in analyzing the video data to determine actual distances. The tape strips are additionally provided with identification markings identifying the type of surfaces and the teeth to which the tape strips are attached. Slots are provided for facilitating observation and digitization of tooth surface data, the side walls of the slots also serving as shoulders for guiding a contour tracing instrument. Various devices are disclosed for facilitating the attachment of the tape strips to the tooth surfaces.

19 Claims, 10 Drawing Sheets

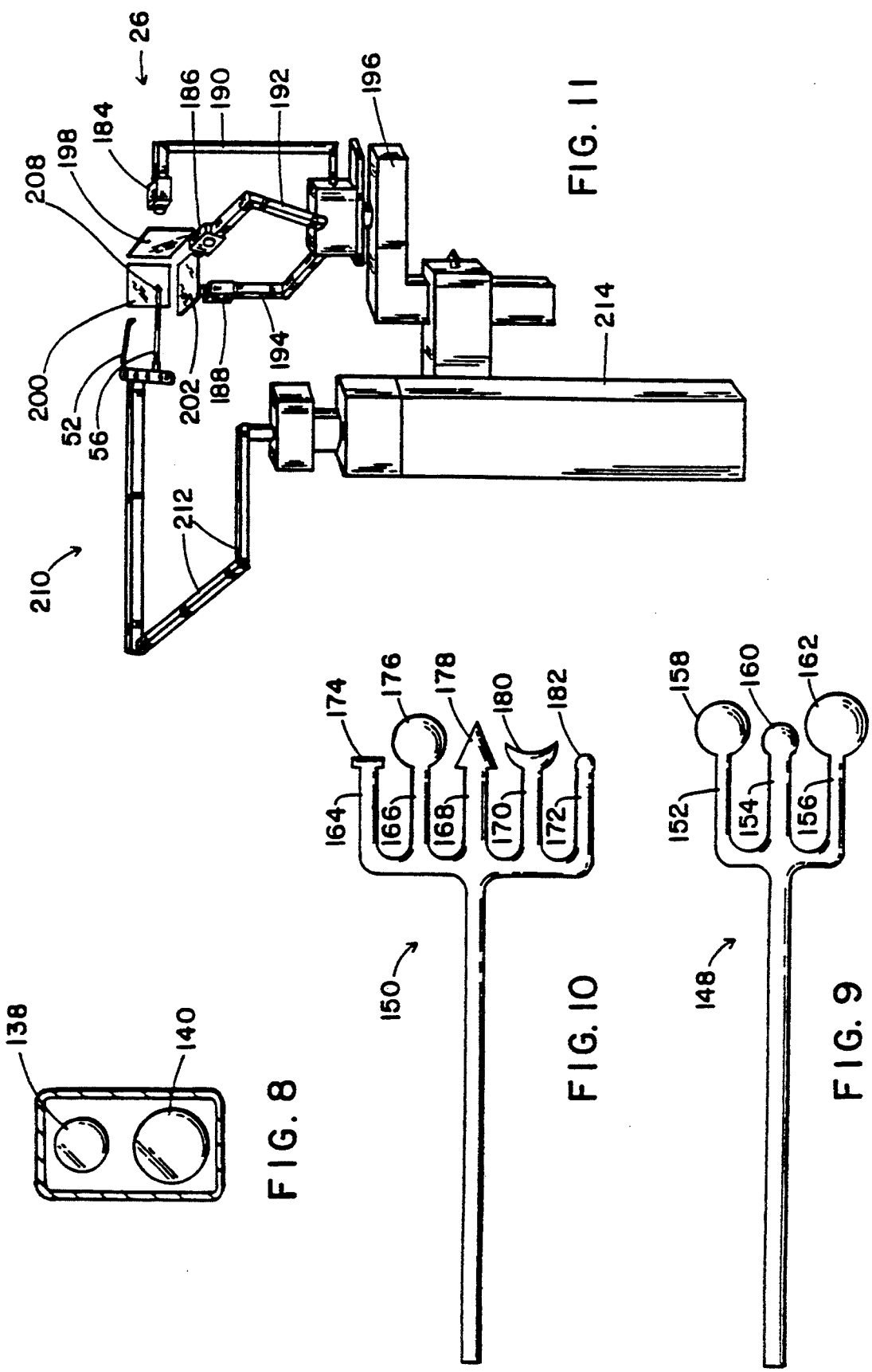

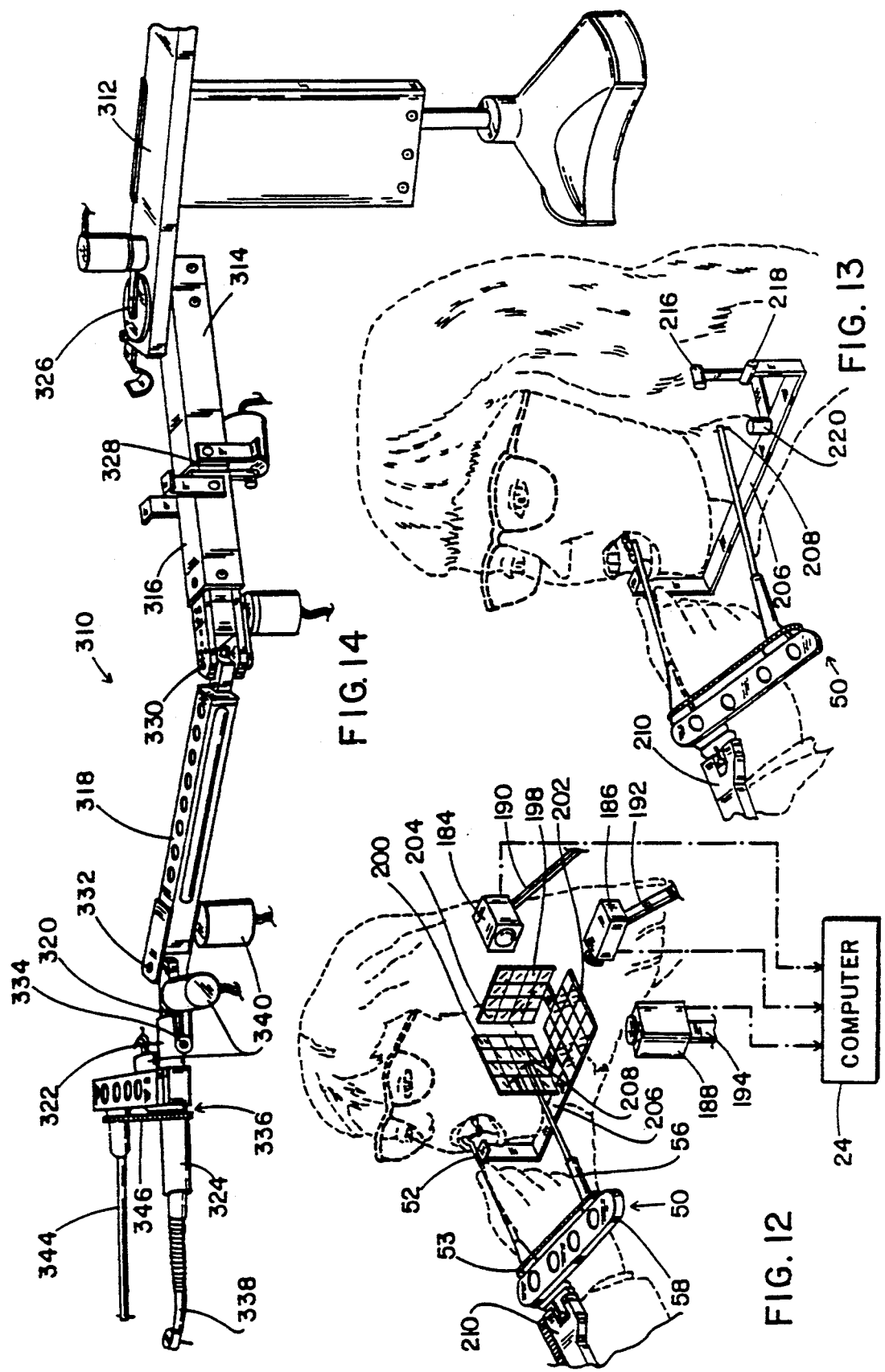

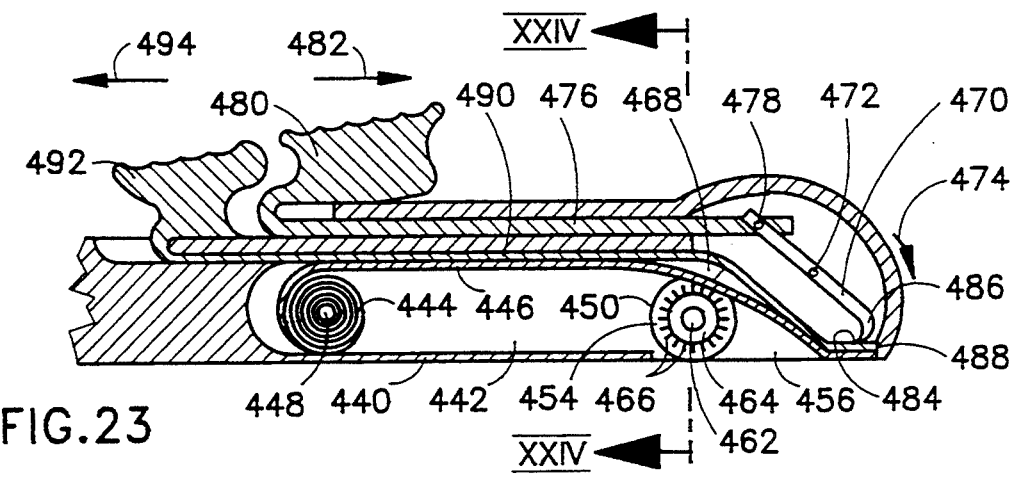
FIG.23
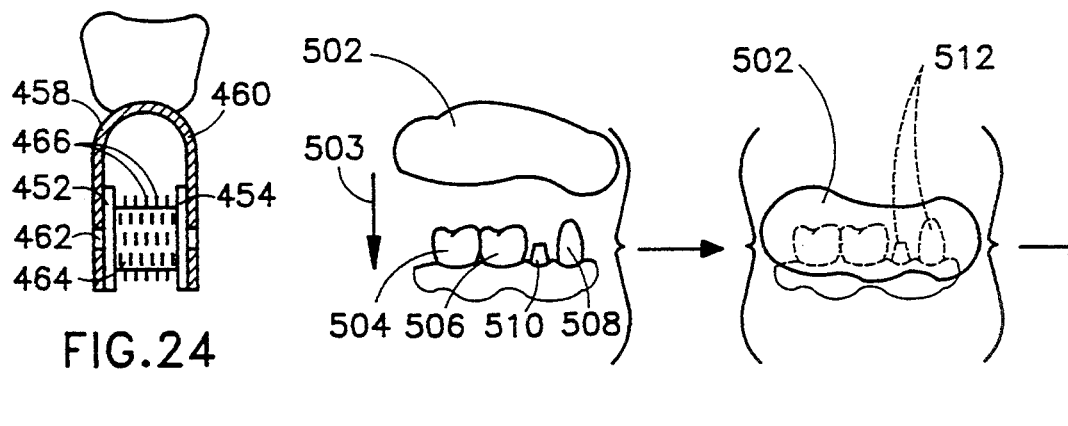
FIG.24
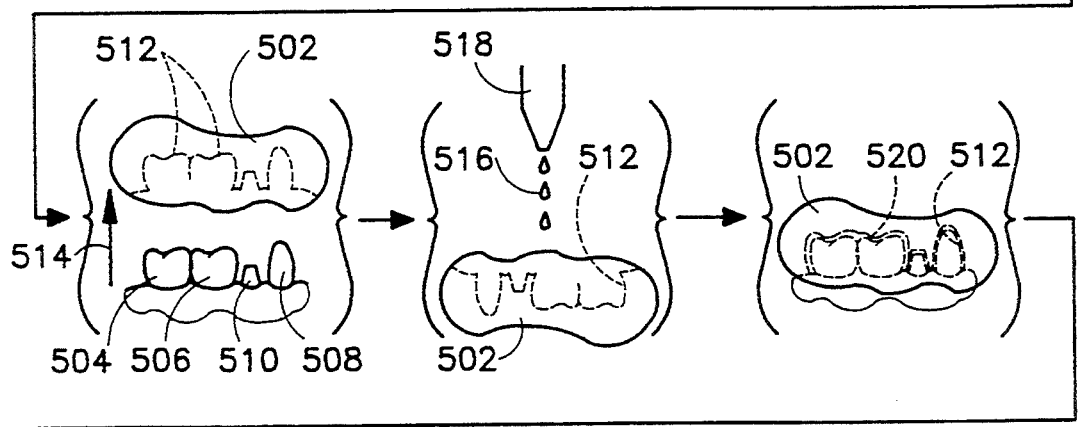
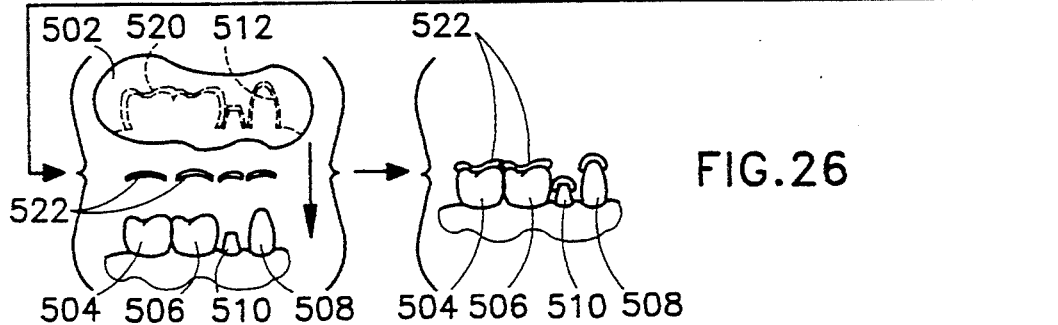
FIG.26

METHOD USING REFERENCE INDICIA ON TAPE ATTACHED TO MOUTH SURFACE TO OBTAIN THREE DIMENSIONAL CONTOUR DATA

CROSS-REFERENCE TO A RELATED APPLICATION

This application is a continuation-in-part of application Ser. No. 507,162 filed Apr. 10, 1990.

FIELD OF THE INVENTION

This invention relates to methods and devices for facilitating the collection of three-dimensional surface data. More particularly, this invention relates to methods and devices for providing a reference distance at a contoured surface for enabling the gathering of surface data via an optical sensing system. This invention also particularly relates to a method and a device for enabling or facilitating the collection of contour data which is used by a computer to generate a three-dimensional representation of the traced surface.

The methods and devices of the instant invention find particular application in the field of dentistry where three-dimensional surface information of a patient's dentition is used in diagnostic and therapeutic procedures implemented with the aid of a computer.

BACKGROUND OF THE INVENTION

In using opto-electronic transducers such as charge-coupled devices ("CCDs") to obtain three-dimensional video-type data of a patient's tooth structure and in using that data to control tooth preparation and even the preparation of dental prostheses for attachment to the tooth, it is helpful and generally necessary for a computer to be provided with exact dimensions of the tooth. In brief, the video data pertaining to the tooth surface structure is best provided with a distance reference at the tooth surface. Such a distance reference enables the computer operating on the three-dimensional surface data to calculate exact dimensions of various tooth features.

Three-dimensional surface data may also be gathered by tracing the surface(s) of the tooth along a multiplicity of contours. The contour data is then automatically fed to a computer for use in generating an eletronically implemented three-dimensional representation of the tooth surface.

It has been found that such contour data is utilizable by conventional CAD/CAM programming only with significant difficulty unless the contour data comprises sets of parallel contours along the tooth surface.

OBJECTS OF THE INVENTION

An object of the present invention is to provide a method and an associated device for providing one or more reference distances at a surface to enable or facilitate the collection of three-dimensional surface data via optical techniques.

Another object of the present invention is to provide such a method and device which facilitates processing of the three-dimensional surface data for different teeth in a patient's mouth.

Another, more particular, object of the present invention is to provide such a method and device which is easy to apply to a mouth surface of a particular patient.

Yet another object of the present invention is to provide a method and an associated device for enabling the collection of contour data from a surface of a three-dimensional object along a plurality of parallel contour lines.

A further object of the present invention is to provide such a method and device which is easy to use.

SUMMARY OF THE INVENTION

A method for generating an electronic representation of a contoured surface comprises, in accordance with the present invention, the steps of (a) providing an applicator member carrying a predetermined pattern of reference marks, (b) at least temporarily affixing the applicator member to the contoured surface, (c) upon affixing of the applicator member to the surface, optically scanning the surface to provide video information of the surface, and (d) using reference information provided by the reference marks and contained in the video siganl to produce the electronic representation of the surface.

Pursuant to another feature of the present invention, the reference marks include identification marks encoding information pertaining to characteristics of the surface.

Where the contoured surface is a mouth surface, the identification marks include a coded identification of a tooth on which the mouth surface is located. The identification marks may also include a coded identification of a position of the surface relative to the tooth and coded information as to other teeth in a patient's jaw, for example, teeth to either side of the subject tooth or on the opposing jaw.

Pursuant to another feature of the present invention, the applicator member takes in part the form of a deformable flexible web having an adhesive layer on at least one side.

Where the contoured surface is a mouth surface, the step of affixing advantageously comprises the step of providing an applicator device having an applicator surface conforming at least substantially to the mouth surface and further comprises the step of using the applicator surface of the applicator device to press the web onto the mouth surface so as to conform the web to the mouth surface and so as to attach the adhesive layer to the mouth surface.

In accordance with a specific implementation of the invention in dental applications, the step of providing the applicator device includes the step of making an impression of the mouth surface with a deformable material. More specifically, the deformable material is a piece of wax and the step of making includes the steps of pressing the piece of wax against the mouth surface and removing the wax from the mouth surface, while the step of providing the applicator device further includes the steps of coating with a hardenable liquid or semi-solid material an impression surface of the piece of wax upon removal thereof from the mouth surface. The liquid material is allowed to harden on the impression surface, whereby the applicator surface constitutes a surface of the hardened liquid material. Even more particularly stated, the wax is pressed against the mouth surface so that the hardenable liquid material is in contact with the mouth surface; the wax together with the hardened liquid material is then removed from the mouth surface upon hardening of the liquid material.

Pursuant to this specific implementation of the invention, the applicator device is used by (a) placing the web onto the hardened liquid material upon removal of the wax and the hardened liquid material from the mouth surface, and (b) pressing the web against the mouth surface via the hardened liquid material. Alternatively, the applicator device is used by (a) placing the web onto the mouth surface upon removal of the wax and the hardened liquid material from the mouth surface, and (b) pressing the web against the mouth surface via the hardened liquid material.

Pursuant to a further feature of the present invention, the flexible web incorporating the reference marks has a preformed shape at least partially conforming to the contoured surface.

Where the surface is a prepared tooth surface, the web advantageously has a shape at least partially conforming to a tooth restoration surface. For example, the web may be in the form of a crown. In that case and others, the web has a concave surface, and the method further comprises the steps of applying a hardenable plastic filler material to the concave surface, positioning the web with the hardenable plastic filler material on the restoration surface, shaping the hardenable plastic filler material and the web to assume a desired tooth restoration surface, and allowing the hardenable plastic filler material to harden.

Pursuant to yet another feature of the present invention, the web is provided with apertures, for example, in the form of slits extending parallel to one another.

Pursuant to still another feature of the present invention, the web is preformed to have a shape conforming at least partially to the mouth surface, whether an original tooth, gum or palate surface or a preparation surface.

In accordance with a specific feature of the invention, reference marks have predetermined dimensions and intermark spacings.

The present invention is directed in part to a device for providing a reference distance at a contoured surface which is optically scanned to provide video information of the surface for generating an electronic representation of the surface. The device comprises a web having a main body of a predetermined substantially uniform thickness, a predetermined pattern of reference marks on the web, including identification marks encoding information pertaining to characteristics of the surface and means for at least temporarily affixing the web to the surface.

Where the surface is a mouth surface, the identification marks include a coded identification of a tooth on which the mouth surface is located. The identification marks may also include a coded identification of a position of the surface relative to the tooth, as well as information as to other teeth in a patient's jaw. The means for temporarily affixing the web to the contoured surface advantageously include an adhesive layer on at least one side of the web. The web may also be provided with a plurality of apertures of at least one predetermined size. Such apertures facilitate scanning of the actual mouth (e.g., tooth) surface by permitting the collection of video data as to the tooth surface itself. Alternatively or supplementally, the web is provided with a plurality of parallel elongate ridges defining a like plurality of parallel shoulders for guiding a dental surface tracing device.

Another device in accordance with the present invention for providing a reference distance at a contoured surface which is optically scanned to provide video information of the surface for generating an electronic representation of the surface comprises a web having a main body of a predetermined substantially uniform thickness, the main body having a predetermined shape at least partially conforming to the contoured surface. A predetermined pattern of reference marks is provided on the web which is further provided with means for at least temporarily affixing the web to the contoured surface.

Yet another device in accordance with the present invention for providing a reference distance at a contoured surface comprises a frame, a supply on the frame for providing a supply of a flowable marking material, a holder attached to the frame for enabling manipulation of the frame, and an applicator attached to the frame and communicating with the supply for applying the marking substance to the surface along a plurality of parallel lines, the applicator including a plurality of applicator elements extending parallel to each other and disposed on the frame in a linear array.

Pursuant to another feature of the present invention, each of the applicator elements includes means for automatically changing a point of application of the respective applicator element in response to pressure exerted on such applicator element at the point of application.

A method for collecting contour information of a three-dimensional surface comprises, in accordance with the present invention, the steps of providing an applicator member formed with a plurality of parallel shoulders, affixing the applicator member to the three-dimensional surface so that the shoulders extend parallel to the surface, placing a distal tip of a probe in contact with each of the shoulders in a sequence, guiding the probe tip along each of the shoulders, and, during the step of guiding, automatically feeding data to a computer as to the position of the probe tip.

Pursuant to another feature of this method in accordance with the present invention, the applicator member takes the form of a deformable web having an adhesive layer on at least one side, while the parallel shoulders are formed by a plurality of parallel slots in the web. Pursuant to an alternative, the parallel shoulders are formed by a plurality of parallel ribs on the web.

Pursuant to yet another feature of the present invention, the applicator member has a predetermined color and the method further comprises the step of automatically changing the color of the applicator member along lines where the applicator member has been contacted by the probe tip. Specifically, the probe tip is provided with means for changing the color of the applicator member along lines where the applicator member has been contacted by the probe tip.

An associated device for use in collecting contour information of a three-dimension surface comprises, in accordance with the present invention, a web having a main body of a predetermined substantially uniform thickness, guides on the web for guiding a tip of a probe instrument along a plurality of paths extending parallel to one another and to the three-dimensional surface, and means on the web for at least temporarily affixing the web to the surface. The guides include a plurality of elongate apertures in the web or, alternatively, a plurality of elongate ribs on the web. In addition, the web may be provided with a predetermined pattern of reference marks on the web, including identification marks encoding information pertaining to characteristics of the tooth surface. It is advantageous if the web is preformed to have a shape conforming at least partially to the surface.

In a method for obtaining data as to a contoured surface of a three-dimensional object, a method for facilitating the collection of such data comprising, in accordance with the present invention, the steps of providing a deformable flexible web having an adhesive layer on at least one side, providing an applicator device having an applicator surface conforming at least substantially to the contoured surface, and using the applicator surface of the applicator device to press the web onto the contoured surface so as to conform the web to the contoured surface and so as to attach the adhesive layer to the contoured surface.

Pursuant to another feature of the present invention, the step of providing the applicator device includes the step of making an impression of the contoured surface with a deformable material. Where the contoured surface is a mouth surface, the deformable material is preferably a piece of wax and the impression is made by pressing the piece of wax against the mouth surface and removing the wax from the mouth surface. The applicator device is further formed by coating with a hardenable liquid material an impression surface of the piece of wax upon removal thereof from the mouth surface and allowing the liquid material to harden on the impression surface. In that case, the applicator surface constitutes a surface of the hardened liquid material.

In allowing the hardenable liquid material to solidify, the wax is pressed against the mouth surface so that the hardenable liquid material is in contact with the mouth surface. The wax and the hardenable liquid or plastic material are removing from the mouth surface upon hardening of the liquid material.

In applying the deformable web to the mouth or tooth surface, the web may be placed first on the tooth surface or, alternatively, on the impression surface of the applicator device.

A method and a device in accordance with the present invention for providing one or more reference distances at a surface to enable or facilitate the collection of three-dimensional surface data via optical techniques facilitates processing of the three-dimensional surface data for different teeth in a patient's mouth by incorporating in the device, which is attached to the patient's tooth surface, a code identifying the tooth surface, the tooth, and the relationship of other teeth in the vicinity of the subject tooth in the patient's mouth.

The device is easy to apply to a tooth surface of a particular patient and is inexpensive to manufacture.

A method and an associated device for enabling the collection of contour data from a surface of a three-dimensional object by guiding a tracing instrument such as a dental probe along a plurality of parallel contour lines. The contour data is thus easy to process by conventional CAD/CAM programs.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is a perspective view of another contour data generating device usable in a dentistry system.

FIG. 23 is a longitudinal cross-section view of a marking tape applicator device in accordance with the present invention.

FIG. 24 is a transverse cross-sectional view taken along line XXIV—XXIV in FIG. 23.

FIG. 26 is a diagrammatic flow chart representing successive steps in the attachment of reference marker tape strips to tooth surfaces, in a procedure in accordance with the present invention.

DETAILED DESCRIPTION OF THE INVENTION

Figure 1:
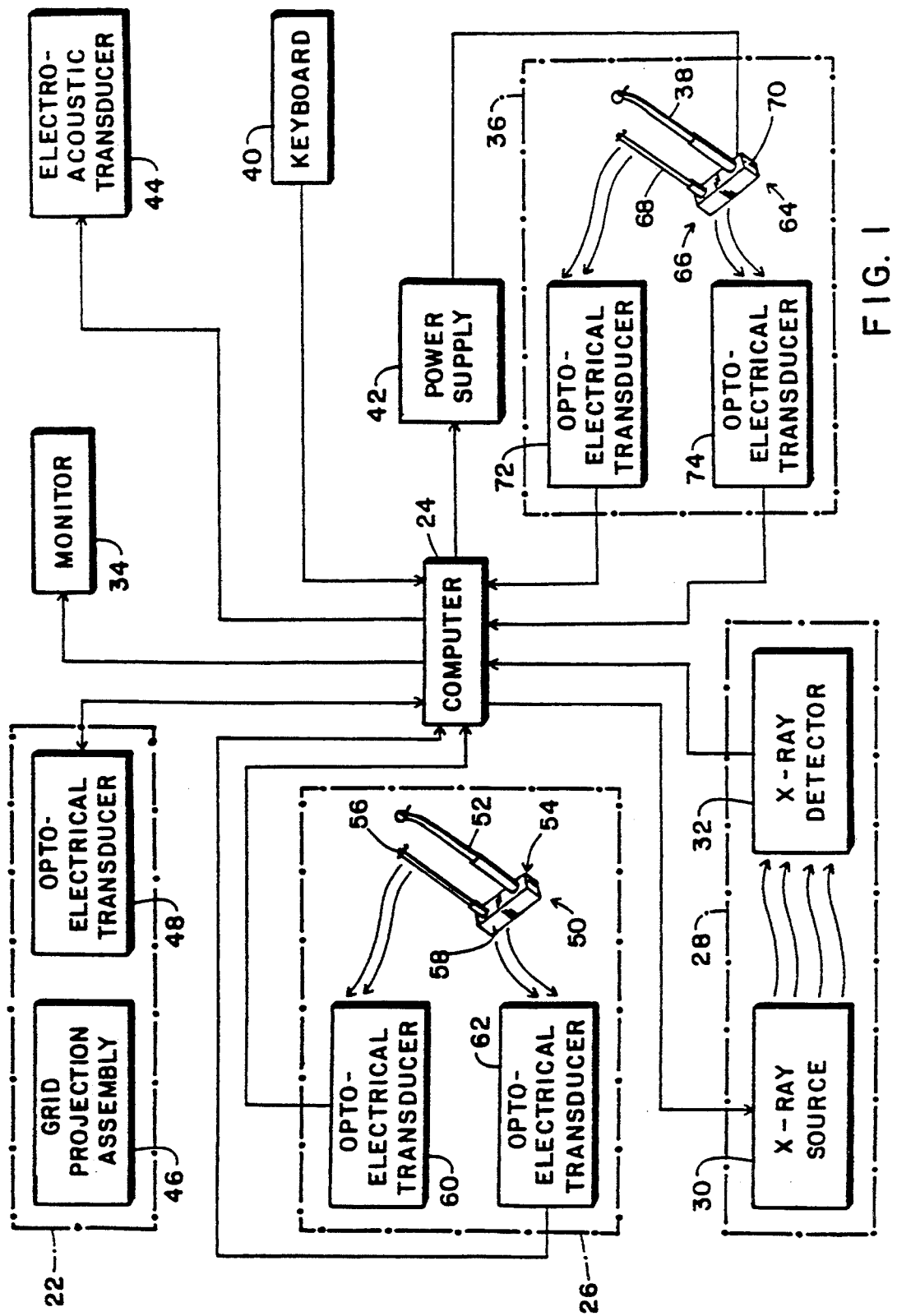
FIG. 1 is a block diagram of a system effecting a desired modification in the shape of a pre-existing object such as a tooth to which access is restricted, in accordance with the present invention.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a contoured surface of an object such as a tooth. A second data generating device or assembly 26 is operatively connected to computer 24 for transmitting thereto digitized signals containing information pertaining to a curvilinear contour on the surface of the contoured surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data strem fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or or to remove an outer layer of the tooth (in the case of preparing a form/shape for a crown or other prosthetic restoration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although the preferred embodiments of the present invention incorporate an optical grid, it is to be appreciated that the invention also conemplates that a grid may be imposed onto the tooth surface by other methods, such as adhesively attaching to the tooth surface a transparency provided with a grid.

As further depicted in FIG. 1 and described in detail hereinafter, data generating device 26 comprises a pantograph-type component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programmed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

In a preferrred embodiment of the invention, data generating device 36 is the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
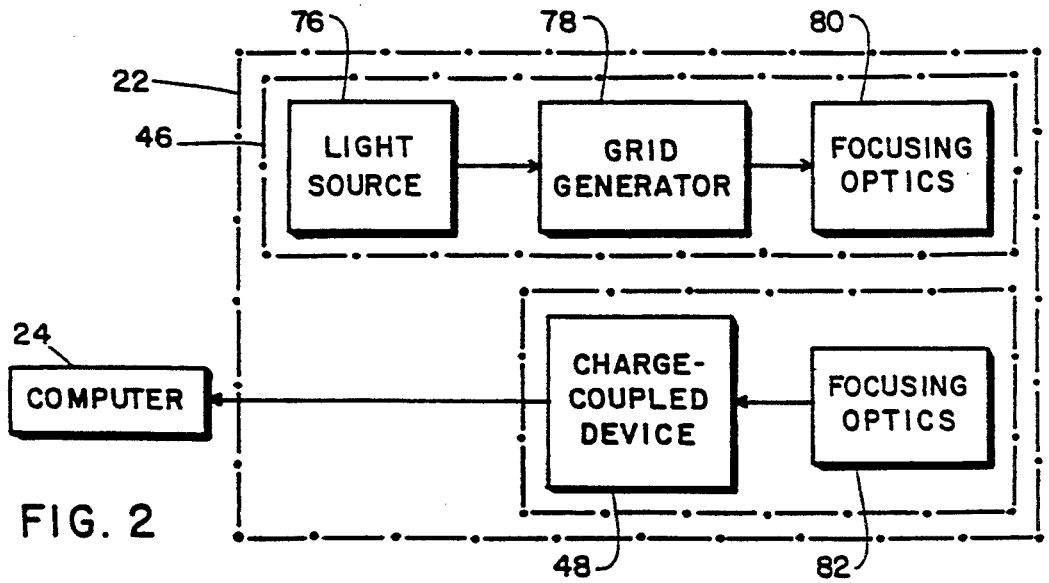
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer 24 to calculate the dimensions of the subject tooth and to display the tooth's structure in a three-dimensional graphic representation on monitor 34.

Figure 3:
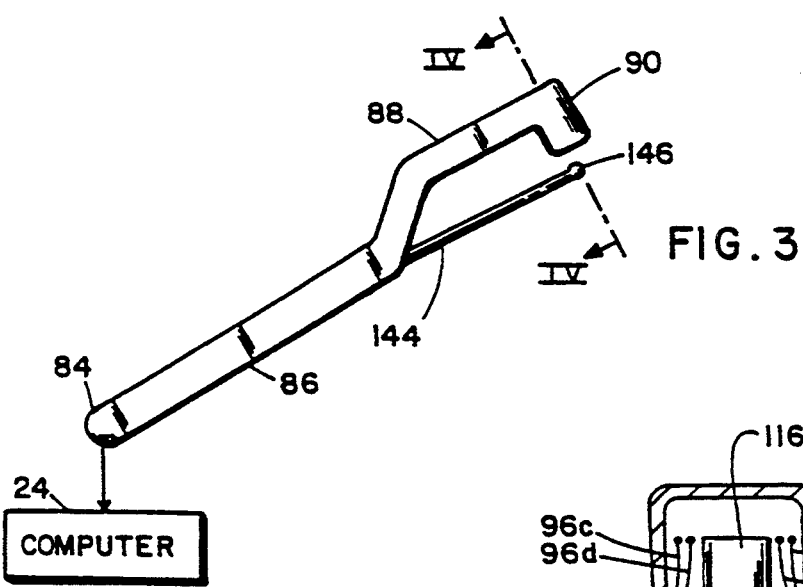
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
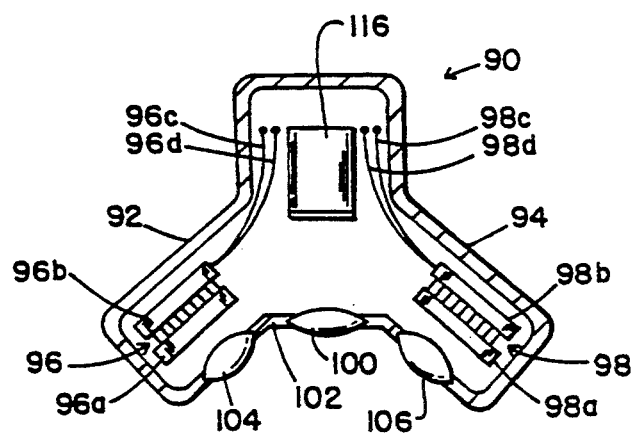
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitve sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
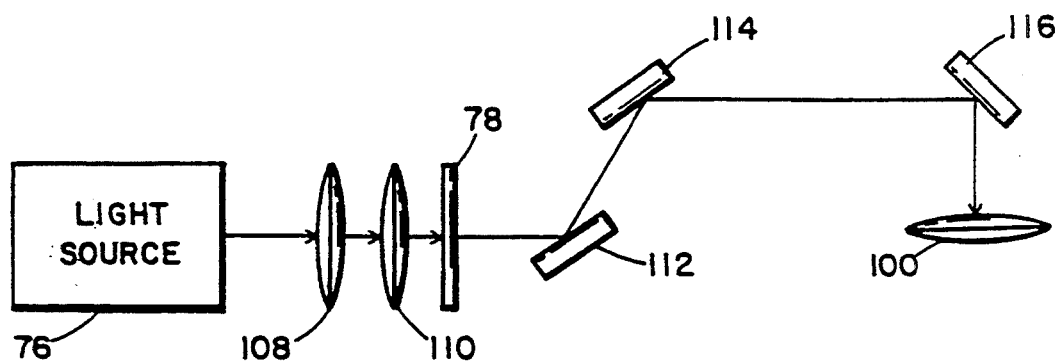
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112,114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
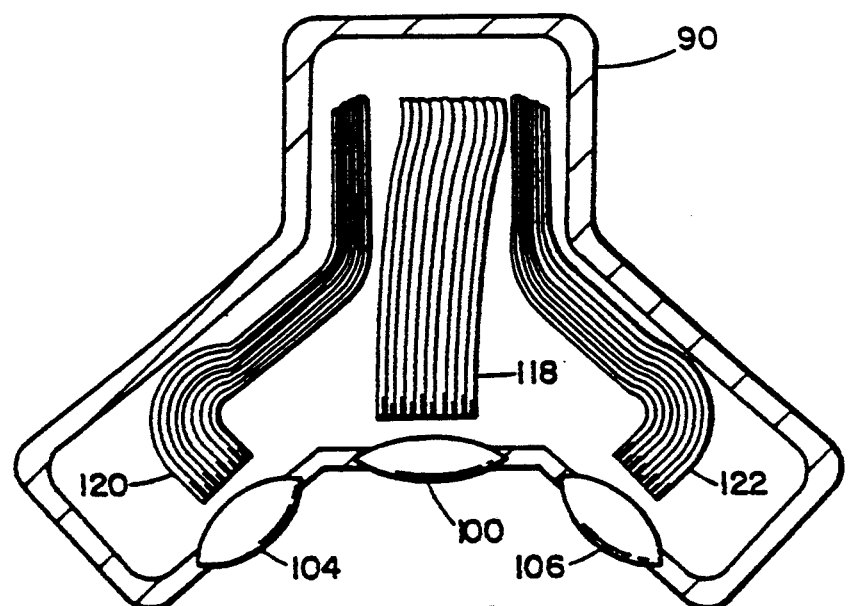
FIG. 6 is a cross-sectional view, similar to FIG. 4, of another particular embodiment of the surface data generating device of FIG. 2.

It is within the contemplation of the invention that the grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
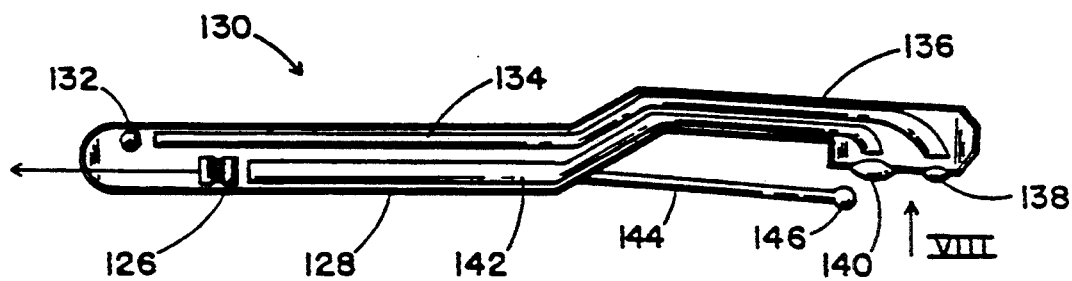
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels correpsonding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises, in a preferred embodiment of the present invention, three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment of the invention, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314–324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326–336 is formed to have sufficient friction to allow the joint to hold a position once placed therein. However, the friction of each joint is low enough so that movement of the joint can be commenced fairly easily.

A plurality of digital encoders 340 are mounted to arm segments 314–324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
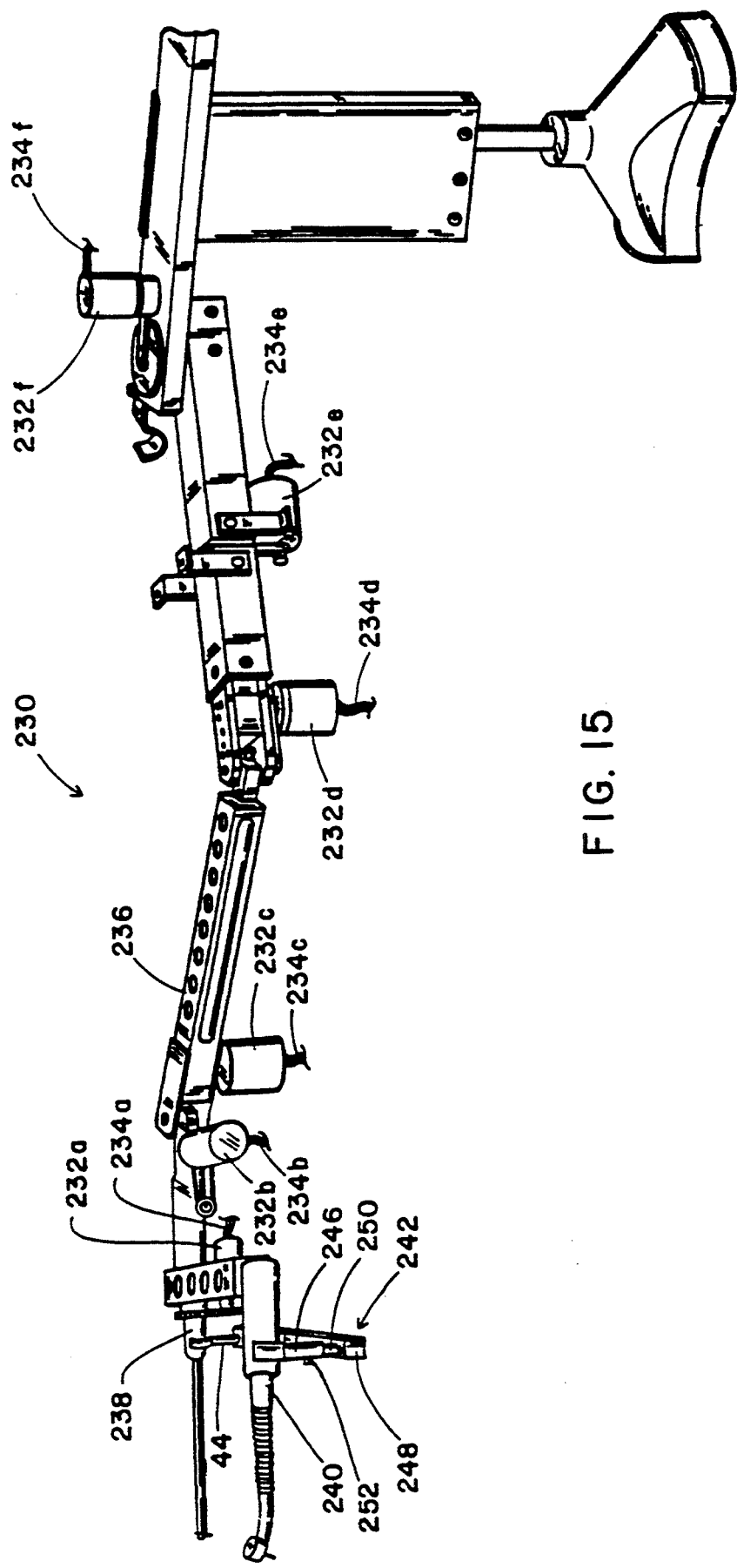
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
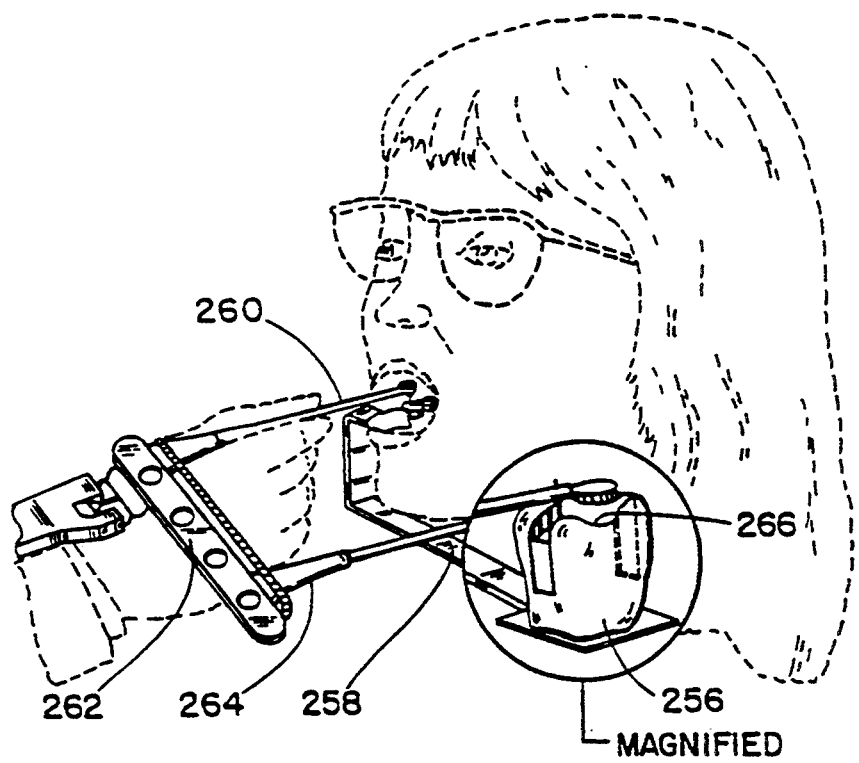
FIG. 16 is a partial perspective view, on an enlarged scale, of a drill movement restriction assembly, showing a tooth preparation preform on an even larger scale.

Limiting the motion of a dentist's drill 254 may be accomplished, in accordance with another feature of the invention shown in FIG. 16, by selecting a tooth preparation preform 256 from a kit of preforms. Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, pursuant to a particular feature of the invention, a kit is provided of dental preparation preforms in different sizes and shapes. Some preforms correspond to inlays such as that shown in FIG. 16. Other preforms corresponding to onlays or crowns. The kit may also include prefabricated restorations, that is, preformed inlays and onlays for attachment to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective restorative inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
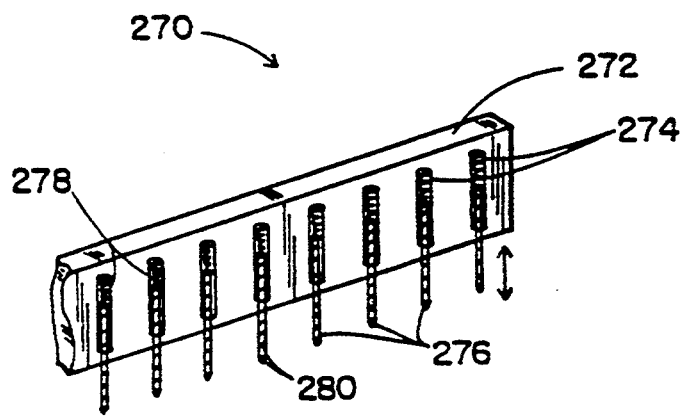
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

Figure 18:
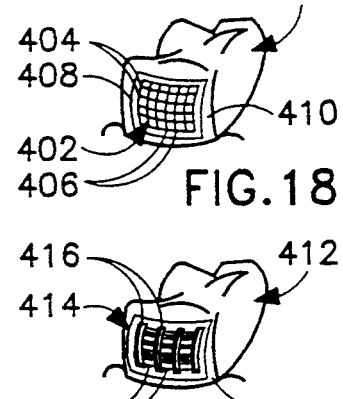
FIG. 18 is a schematic perspective view of a tooth to which a reference marking strip has been applied in accordance with the present invention.

FIG. 18 illustrates one method of applying reference markings to the surface of a tooth or tooth preparation for purposes of providing a distance standard for data generating device 22 (FIG. 1). The reference markings in this case take the form of a grid 402 of a first set of parallel lines 404 and a second set of parallel lines 406, the first set being substantially orthogonal to the second set. Grid 402 is printed or otherwise disposed on a strip or tape 408 which is attached to a surface 410 (e.g., a buccal surface) of a tooth 412 (e.g., a molar) via a layer of adhesive (not shown).

Figure 19:
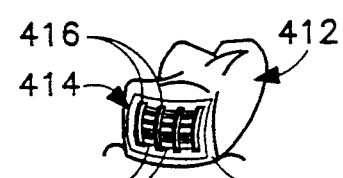
FIG. 19 is a schematic perspective view of the tooth of FIG. 18, with a different reference marking strip in accordance with the present invention.

FIG. 19 shows, on surface 410 of tooth 412, another reference marker applicator in the form of a tape strip 414 provided with a plurality of transversely extending slits 416 and, between the slits, with identification markings 418 in the form of bar codes. Slits 416 are of identical size and orientation and are spaced from one another by a known distance. In addition, because tape strip 414 has a uniform thickness, the depth of slits 414 is known. The known depth of slits 414 provides a particularly precise reference distance at the surface 410 of tooth 412. Furthermore, identification markings 418 serve to automatically provide computer 24, via data generating device 22, with information pertaining to the type of tooth (molar) and the surface (buccal), as well as the location of tooth 412 in the patient's mouth and perhaps also the relative location with respect to a tooth or teeth to be restored.

Figure 20:
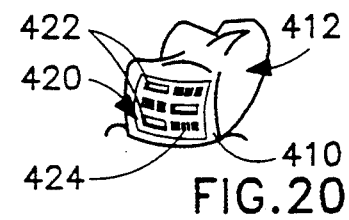
FIG. 20 is a schematic perspective view of the tooth of FIGS. 18 and 19, with another reference marking strip in accordance with the present invention.

FIG. 20 depicts, again on surface 410 of tooth 412, yet another reference marker applicator similar to that illustrated in FIG. 19. In FIG. 20, the reference marker applicator is a tape strip 420 provided with a plurality of relatively staggered, longitudinally extending slits 422 and, between the slits, with identification markings 424 in the form of bar codes. Slits 422 are preferably of identical size and orientation and are spaced from one another, both in the transverse direction and the longitudinal direction, by known distances. In addition, because tape strip 420 has a uniform thickness, the depth of slits 422 is known. The known depth of slits 422 again provides a precise reference distance at the surface 410 of tooth 412. As described hereinabove, the identification markings 424 serve to automatically provide computer 24, via data generating device 22, with information as to the tooth type, surface, location in the patient's mouth and with respect to a projected restoration.

Figure 21:
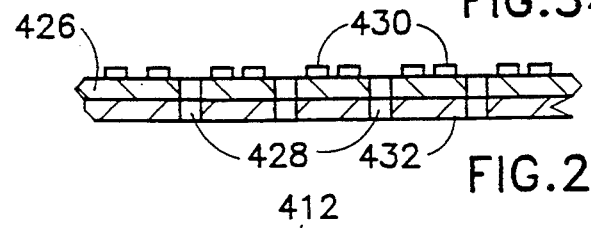
FIG. 21 is a longitudinal cross-sectional view of another reference marking strip in accordance with the present invention.

A tape strip 426 with slits 428 and reference markings 430 is shown in exagerrated detail in FIG. 21. Also illustrated in that drawing figure is an adhesive layer 432 for temporarily fixing the tape strip 426 to a mouth surface. It is to be noted that tape strip 426, as well as any other similar tape strip or reference mark applicator described herein, may be applied to gum and palate surfaces instead of to original tooth or restoration surfaces. In such a case, the identification markings carried on the tape are appropriate to the surface to which the reference marking application is being attached.

Figure 22:
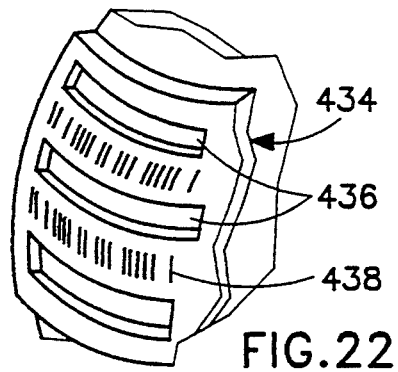
FIG. 22 is a partial perspective view, on an enlarged scale, of yet a further reference marking applicator strip in accordance with the present invention, showing the strip applied to a tooth surface.

As illustrated in FIG. 22, yet another reference marking applicator comprises a tape strip 434 provided with a plurality of longitudinally extending slits 436 and, between the slits, with identification markings 438 in the form of bar codes. Slits 436 are preferably of identical size and orientation and are spaced from one another, both in the transverse direction and the longitduinal direction, by known distances. Tape strip 434 has a uniform thickness; consequently, the depth of slits 436 is known and can be programmed or entered into computer 24. The known depth of slits 436 thus provides computer 24 with an exact reference distance. As described hereinabove, the identification markings 424 serve to automatically provide computer 24, via data generating device 22, with information as to the tooth type, surface, location in the patient's mouth and with respect to a projected restoration.

As shown in FIGS. 23 and 24, a device for facilitating the attachment of a reference tape such as tape 408, 414, 420, or 426 to a surface (e.g., buccal surface 410) of a tooth (e.g., molar 412) comprises an elongate body 440 formed at a distal end with a chamber 442. Chamber 442 houses at a proximal end a roll 444 of reference marking applicator tape 446, the roll being rotatably secured to body 440 by a shaft 448. Body 440 may be provided with a door (not illustrated) for facilitating the replacement of tape roll 444 with another roll of the same kind of tape (e.g., the same identification markings) or a roll of a different kind of tape. Alternatively, the device may include means for attaching a cartridge, wherein different cartridges hold tapes for different applications, such as for different mouth surfaces.

Figure 34:
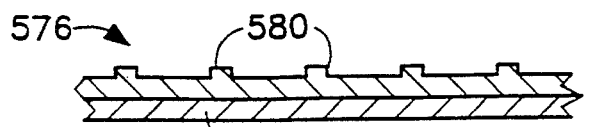
FIG. 34 is a cross-sectional view of a tape strip for facilitating tracing of a tooth contour, in accordance with the present invention.

As further shown in FIGS. 23 and 34, a distal end of chamber 442 contains a tape gripping and transport mechanism 450. Mechanism 450 includes a pair of wheels 452 and 454 (FIG. 24) which project slightly through an opening 456 in body 440 at the distal end of chamber 442. Wheels 452 and 454 are rotatably mounted to side walls 458 and 460 of body 440 via a shaft 462 and are rigid with respect to a cylinder 464 in which a plurality of pins 466 are embedded. During a movement of the distal end of the instrument or device across a mouth surface, pins 466 grippingly engage tape 446. Rotation of wheels 452 and 454, caused by friction contact with a relatively moving mouth surface, causes cylinder 464 to rotate and pins 466 to pull tape 446 from roll 444 towards the distal end of the instrument. Tape 446 is wedged between spiked cylinder or roller 464 and a contoured internal piece 468.

Distally of tape transport mechanism 450, tape 446 is pressed against a mouth surface through the action of a lever arm 470 rotatably secured to body 440 via a pivot pin 472. Lever arm is rotated in the direction indicated by an arcuate arrow 474, in response to a distally directed movement of an actuator strip 476. Actuator strip 476 is pivotably secured at a distal end to lever arm 470 at 478 and is attached at a proximal end to an actuator knob 480. Manual pressure on actuator knob 480 in the direction of arrow 482 causes a swinging of lever arm 470 so that a sharpened tip or edge 484 at the free end 486 of the lever arm contacts one side of a plate 488. A free end of tape 446 is located on the other side of plate 488, whereby application pressure is applied to tape 446 via lever arm 470 and plate 488. Plate 488 is integral with a distal end of a preformed spring metal strip 490 in turn connected at a proximal end to a second actuator knob 492.

Upon the application of a length of tape 446 to a tooth surface, actuator knob 492 is manually pulled in the direction of arrow 494, thereby removing plate 488 from between the tape and the sharpened tip or edge 484 of lever arm 470. Actuator knob 480 is then pushed in the distal direction, as indicated by arrow 482, to pinch tape 446 at the distal end thereof against the tooth surface. This pinching action results in a severing of the free end of tape 446 by sharp edge 484. Upon the completion of the tape cutting operation, actuator knob 492 is pushed back in the distal direction, whereupon the applicator instrument is ready for another tape application operation.

Figure 25:
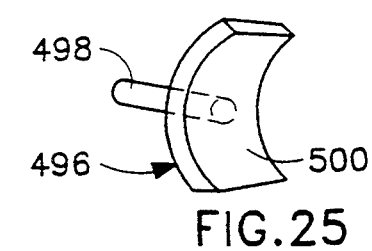
FIG. 25 is a perspective view of a marking tape applicator element in accordance with the present invention.

FIG. 25 shows a simpler device for use in applying a strip of reference marker bearing tape (e.g., tape 426 in FIG. 21) to a tooth or gum surface. The applicator device comprises a body portion 496 provided on an outer side with a handle grip 498 and formed on an inner side with an arcuate applicator surface 500 essentially conforming to the tooth, gum or other mouth surface to which the reference marker tape strip is to be applied. A dental practitioner may be provided with a kit of such applicator forms, a plurality of forms being included for each mouth surface. For example, an occlusal or lingual surface of an upper molar or a lower incisor will have on the order of a dozen forms in different sizes and shapes, as will other mouth surfaces.

In using the appicator device or form of FIG. 25, a dentist or technician disposes a tape strip on the curved applicator surface 500 or, alternatively, on the mouth surface to which the tape is to be applied. The tape strip is then pressed against the mouth surface via the applicator form.

It is to be noted that reference marker bearing tape strips in accordance with the present invention may be tinted or otherwise coated with an off-white, gray or a hued coloring in order to reduce glare. The reduction of glare facilitates the input of contour information via data generating device 22.

Successive steps in yet another method for applying reference marker tape strips to teeth and other features in the mouth is illustrated in FIG. 26. A clump of wax 502 or other impression forming material is placed over the mouth surface or surfaces, as indicated by an arrow 503. In the example of FIG. 26, the relevant mouth surfaces include occlusal surfaces of two intact molars 504 and 506 and an intact bicuspid 508, as well as a prepared molar 510. The clump of wax is manipulated so that an impression 512 is taken of the subject tooth surfaces. The wax is then removed, as indicated by an arrow 514. A hardenable liquid dental material 516 from a reservoir 518 is then deposited onto the impression surface 512 of the piece of wax 502. In a subsequent step, the piece of wax 502 is replaced on the teeth so that the hardenable liquid material takes the form of a thin layer 520 conforming to the impression 512 and therefore to the subject tooth surfaces. Upon the hardening of the coating layer 520, the piece of wax 502, with the hardened coating layer 520, is removed (not shown). In a subsequent step, one or more reference marker tape strips 522 are placed between the subject teeth 504, 506, 508 and 510, on the one hand, and the hardened coating layer 520 in the piece of wax 502, on the other hand. As indicated by an arrow 524, the piece of wax 502 is pressed against the tape strips 522 which in turn are pressed against the subject tooth surfaces. Because coating layer 520 has the exact shape of the subject tooth surfaces, tape strips 522 are pressed throughout their entire extent against those tooth surfaces, thereby optimizing adherence of the tape strips to the teeth.

Figure 27:
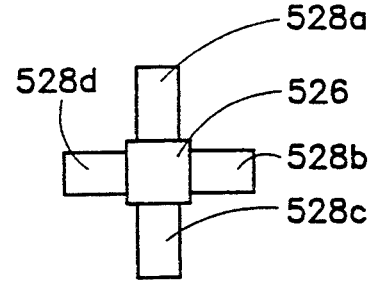
FIG. 27 is a top elevational view of an applicator member for facilitating the provision of distance reference marks and/or identification markings at a mouth surface, in accordance with the present invention.
Figure 28:
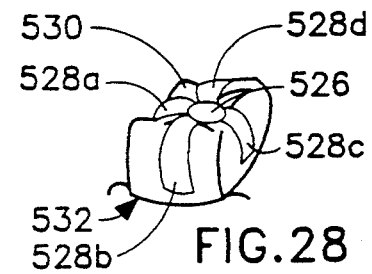
FIG. 28 is a perspective view showing use of the applicator member of FIG. 27 on a tooth.

As depicted in FIG. 27, an applicator member for facilitating the provision of distance reference marks and/or identification markings at a mouth surface comprises a central section 526 having a plurality of appended tape strips 528a, 528b, 528c and 528d connected thereto. As shown in FIG. 28, central section or hub 526 is designed for attachment to a particular tooth surface, such as the occlusal surface 530 of a molar 532, while tape strips 528a, 528b, 528c and 528d are adapted for attachment to different side surfaces, such as an interproximal, a buccal, another interproximal and a lingual surface, respectively. Each tape strip 528a, 528b, 528c and 528d is accordingly provided with slots and identification markings (not illustrated) identifying the respective tooth surface (interproximal, buccal, interproximal and lingual) and the particular tooth (e.g., upper right first molar). Central section or hub 526 is also provided with identifying markings and slots or slits (not shown). A kit of such adhesively attachable cross-, star- or wheel-shaped reference marker elements may be provided for dental practitioners.

Figure 29:
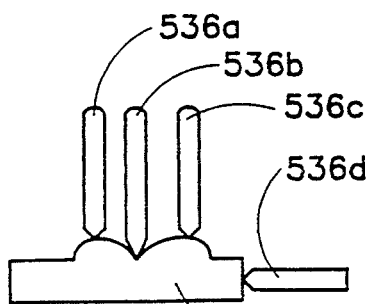
FIG. 29 is a top elevational view of another applicator member for facilitating the provision of distance reference marks and/or identification markings at a mouth surface, in accordance with the present invention.

FIG. 29 illustrates a variation of the reference marker element of FIGS. 27 and 28. In FIG. 29, a thin metallic body member 534 is connected to a plurality of elongate extensions or arms 536a, 536b, 536c, 536d each provided on one side with an adhesive layer and further provided with slits or slots and identification markings (not illustrated), as described above. The reference marker element of FIG. 29 is used by sliding the metallic body member 534 between two adjacent teeth and folding the extensions or arms 536a, 536b, 536c, 536d over occlusal and lingual or buccal surfaces of teeth. Extensions or arms 536a, 536b, 536c, 536d may be pressed to the respective tooth surface by an application member such as that illlustrated in FIG. 25. Alternatively, a conventional dental instrument with a blunt edge may be utilized.

Figure 30:
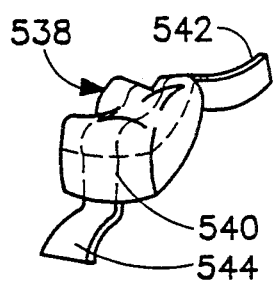
FIG. 30 is a perspective view of device for applying reference markers to the surface of a tooth, in accordance with the present invention.

As shown in FIG. 30, a device for applying reference markers to the surface of a tooth (e.g., a molar) comprises a crown-shaped member 538 formed with a plurality of score lines 540 and one or more tabs 542, 544.

Figure 31:
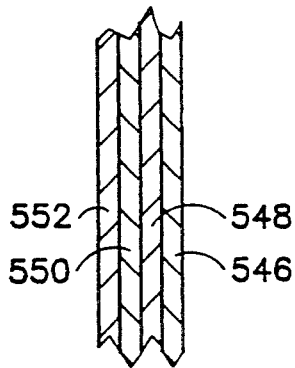
FIG. 31 is a cross-sectional view of a wall of the device of FIG. 30.

As further shown in the cross-sectional view of FIG. 31, crown-shaped member 538 includes an inner adhesive layer 546, a second layer 548 of transparent or translucent polymeric material in which reference distance markings and identification markings (not shown) are embedded, another adhesive layer 550 and an outer layer of polymeric material 552.

Upon the disposition of crown-shaped reference marker applicator member 538 over a similarly shaped tooth and the application of pressure, for example, by means of a blunt dental instrument, to ensure a bond-forming contact between inner adhesive layer 546 and the various surfaces of the tooth, tabs 542 and 544 are pulled, thereby tearing polymeric layer 552 along score lines 540. Inasmuch as adhesive layer 546 is stronger than adhesive layer 550, the tearing of polymeric layer 552 removes that layer from the tooth, while leaving marker bearing strips of layer 548 intact on the tooth surfaces.

It is to be noted that dental practitioners may be provided with kits of such multiple preformed tooth-shaped applicator members for temporarily attaching reference and identification marker elements to tooth surfaces. Each kit includes a plurality of preformed applicators for each tooth, which take into account basic variations in the shape of that tooth as well as different sizes thereof. In using such a kit, the dental practitioner or aide selects the preformed applicator member which is closest in shape and size to the subject tooth. In the event the selected applicator member deviates from an outer surface of the tooth, the applicator member may be deformed by the practitioner to assume the tooth's shape and thereby press the inner adhesive layer 546 against the tooth.

It is to be further noted that marker bearing layer 548 (as well as adhesive layers 546 and 550) may be formed as an array of separate segments each corresponding to a respective tooth surface. The separate segments are held in a predetermined pattern or array by outer polymeric layer 552.

Figure 32:
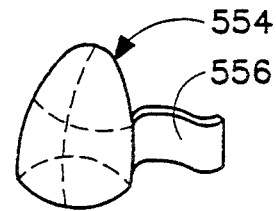
FIG. 32 is a perspective view of a similar device for applying reference markers to the surface of a prepared tooth, in accordance with the present invention.

As shown in FIG. 32, an applicator member 554 may be provided for attaching reference marker strips or segments to surfaces of a prepared tooth. The structure and use of applicator member 554 is similar to that of the applicator member of FIG. 30. Applicator member 554 has a four-part layer structure (see FIG. 31) and at least one pull tab 556 for facilitating the removal of the outer polymeric layer (552, FIG. 31) upon the application of application member 554 to a prepared tooth.

Figure 33:
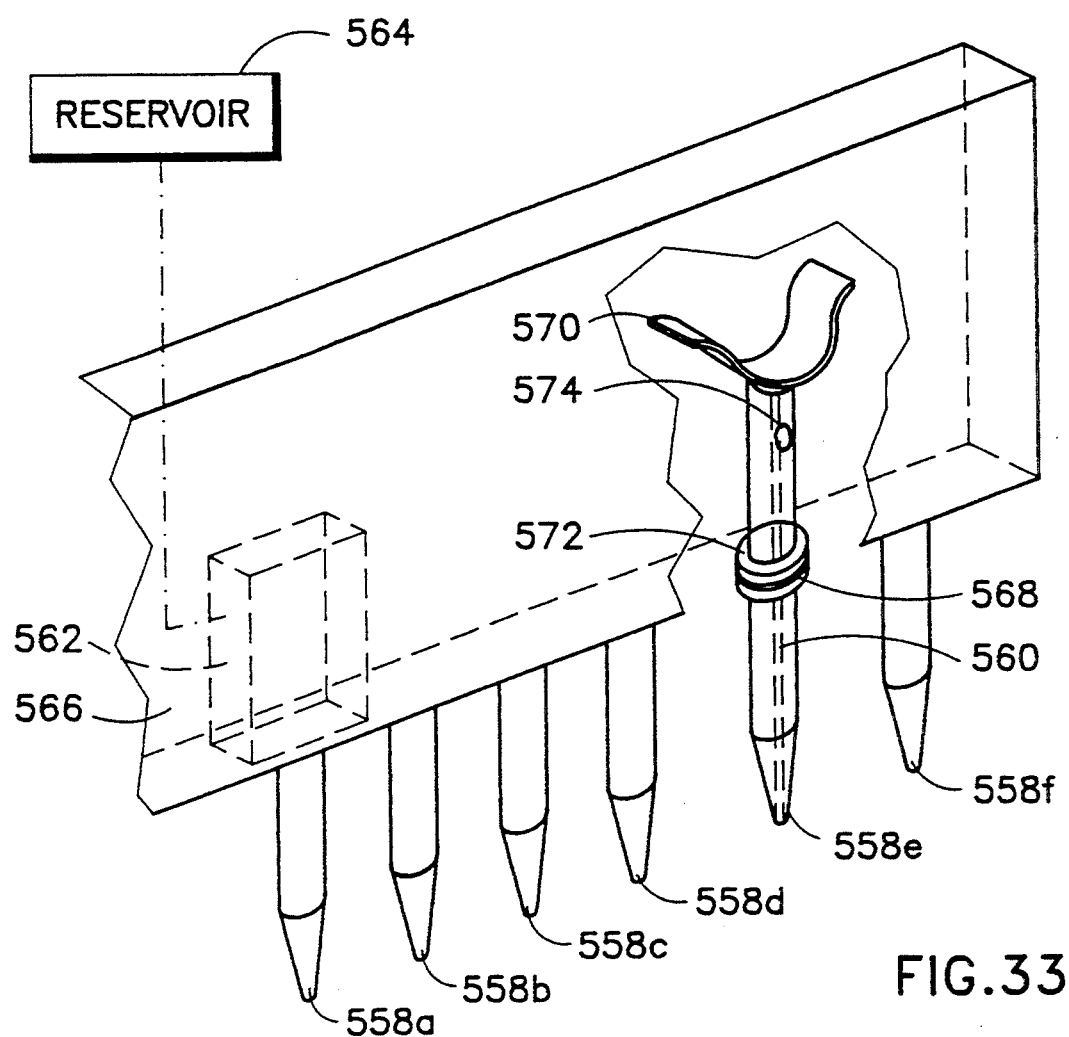
FIG. 33 is a partial perspective view, on an enlarged scale and partially broken away, of another device for applying reference markings to a mouth surface, in accordance with the present invention.

FIG. 33 depicts another device for applying reference markings to a mouth surface. Basically, the device comprises a plurality of elongate pointed applicator members 558a, 558b, 558c, 558d, 558e, 558f each formed with a respective axial channel 560. At an inner end, each pointed member 558a, 558b, 558c, 558d, 558e, 558f is disposed inside a chamber 562 which containing a nontoxic marking fluid replenishable, for instance, from a reservoir or supply 564. Reservoir 564 may be located inside a handle or holder component 566 of the marking device.

Applicator members 558a, 558b, 558c, 558d, 558e, 558f extend parallel to each other and are disposed on holder or frame 566 in a linear array. Accordingly, upon pressing of the tips of the applicator members 558a, 558b, 558c, 558d, 558e, 558f against a mouth surface and upon a movement of the holder or frame 566 generally in a direction perpendicular to the linear array of applicator members 558a, 558b, 558c, 558d, 558e, 558f, a plurality of parallel lines are placed on the moth surface, following the contours thereof.

Applicator members 558a, 558b, 558c, 558d, 558e, 558f are provided with a respective ring seal 568 at the base of the respective fluid containing chamber 562. In addition, each applicator member 558a, 558b, 558c, 558d, 558e, 558f is biased into an outward or extended position by a respective leaf spring 570. The outward motion of each applicator member 558a, 558b, 558c, 558d, 558e, 558f is arrested by a respective collar 572 which engages the respective ring seal 568. Leaf springs 570 ensure that applicator members 558a, 558b, 558c, 558d, 558e, 558f follow the contour of the surface being marked.

Channels 560 each communicate at an inner end with the respective fluid-containing chamber 562 via one or more ports 574, whereby marking fluid flows from chamber 562 to the tips of applicator members 558a, 558b, 558c, 558d, 558e, 558f.

It is to be noted that applicator members 558a, 558b, 558c, 558d, 558e, 558f are essentially spring loaded pens and may be formed as such. For example, each applicator member may be provided with a felt tip or other component for ensuring an appication of ingestible and removable ink to a mouth surface.

Figure 35:
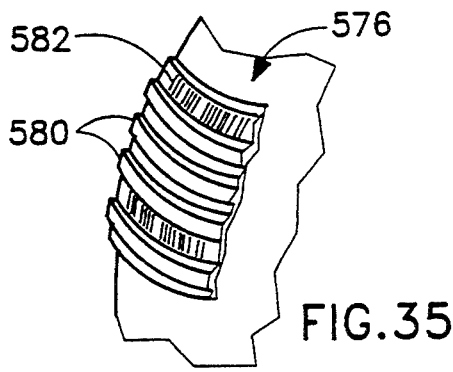
FIG. 35 is a partial perspective view, on an enlarged scale, of the tape strip of FIG. 34 attached to a tooth surface.

As illustrated in FIGS. 34 and 35, a tape strip 576 for facilitating tracing of a tooth contour with pantograph-type data generating device or assembly 26 (FIG. 1) is provided on one side with an adhesive layer 578 and on an opposite side with a plurality of parallel ridges or beads 580 defining a series of parallel shoulder for guiding the tip of stylus member 52 (FIG. 1) along the surface of a tooth or other mouth surface.

As illustrated in FIG. 35, tape strip 576 may be further provided with identification markings 582, as described hereinabove with reference to FIGS. 19–22, for identifying the different mouth surfaces to which the tape strip is applied. Clearly, different rolls of tape strip 576 are provided for different types of tooth surfaces. Thus, a practitioner may be furnished with a kit having several rolls of contour guide tapes for each tooth.

It is to be noted that the slits or slots 416, 422 428 and 436 in reference marker tape strips 414, 420, 426 and 434 (FIGS. 19–22) may function as guides for stylus member 52 of data generating device or assembly 26. The side walls of the slits or slots thus serve as shoulders for guiding the movement of stylus member 52 along a plurality of parallel lines.

It is to be further noted that ridges as in tape strip 576 and slots as in tape strip 22 may be combined in a single tape strip to facilitate both the collection of three-dimensional video data with data generating device or assembly 22 and the collection of three-dimensional contour data with data generating device or assembly 26. Both slots and ridges may extend in the longitudinal direction, with ridges alternating with slots in the transverse direction.

It is within the contemplation of the invention that the techniques and devices described herein may find applications in fields other than the dental industry. For example, the gathering of video and contour information about three-dimensional surfaces is applicable in the machine tool industry.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for generating an electronic representation of a contoured mouth surface, comprising the steps of:

providing an applicator member carrying a predetermined pattern of reference marks having predetermined dimensions and intermark spacings, said applicator member taking the form of a deformable flexible web defining at least one guide shoulder and having an adhesive layer on at least one side;

at least temporarily affixing said applicator member to the contoured mouth surface;

upon affixing of said applicator member to said surface, optically scanning said surface to generate a video signal encoding information as to said surface and said reference marks;

also upon affixing of said applicator member to said surface, guiding a tip of a stylus instrument along said shoulder and concomitantly along said surface;

during said step of guiding, generating contour data as to a location of said tip; and using said contour data and reference information provided by said reference marks and contained in said video signal to produce the electronic representation of the surface.

2. The method set forth in claim 1 wherein said reference marks include identification marks encoding information pertaining to characteristics of said surface.

3. The method set forth in claim 2 wherein said identification marks include a coded identification of a tooth on which said mouth surface is located.

4. The method set forth in claim 3 wherein said identification marks include a coded identification of a position of said surface relative to said tooth.

5. The method set forth in claim 3 wherein said identification marks include coded information as to other teeth in a patient's jaw.

6. The method set forth in claim 1 wherein said step of affixing comprises the step of providing an applicator device having an applicator surface conforming at least substantially to said mouth surface and further comprises the step of employing said applicator surface of said applicator device to press said web onto said mouth surface so as to conform said web to said mouth surface and so as to attach said adhesive layer to said mouth surface.

7. The method set forth in claim 1 wherein said flexible web has a preformed shape at least partially conforming to said surface.

8. The method set forth in claim 7 wherein said web has a shape at least partially conforming to a tooth restoration surface.

9. The method set forth in claim 8 wherein said web has a concave surface, further comprising the steps of applying a hardenable plastic filler material to said concave surface, positioning said web with said hardenable plastic filler material on said a prepared tooth surface, shaping said hardenable plastic filler material and said web to assume a desired tooth restoration surface, and allowing said hardenable plastic filler material to harden.

10. The method set forth in claim 9 wherein said web is preformed to have a shape conforming at least partially to said mouth surface.

11. The method set forth in claim 1 wherein said web is provided with apertures which define a plurality of shoulders for guiding said tip of said stylus.

12. The method set forth in claim 11 wherein said apertures are slits extending parallel to one another.

13. A method for generating an electronic representation of a contoured mouth surface, comprising the steps of:

providing an applicator member carrying a predetermined pattern of reference marks having predetermined dimensions and intermark spacings, said applicator member taking the form of a deformable flexible web having an adhesive layer on at least one side;

at least temporarily affixing said applicator member to the contoured mouth surface;

upon affixing of said applicator member to said surface, optically scanning said surface to generate a video signal encoding information as to said surface and said reference marks;

using reference information provided by said reference marks and contained in said video signal to produce the electronic representation of the surface, said step of affixing comprising the step of providing an applicator device having an applicator surface conforming at least substantially to said mouth surface and further comprising the step of using said applicator surface of said applicator device to press said web onto said mouth surface so as to conform said web to said mouth surface and so as to attach said adhesive layer to said mouth surface.

14. The method set forth in claim 13 wherein said step of providing said applicator device includes the step of making an impression of said mouth surface with a deformable material.

15. The method set forth in claim 14 wherein said deformable material is a piece of wax and said step of making includes the steps of pressing said piece of wax against said mouth surface and removing said wax from said mouth surface, said step of providing said applicator device further including the steps of coating with a hardenable liquid material on an impression surface of the piece of wax upon removal thereof from said mouth surface and allowing the liquid material to harden on said impression surface, said applicator surface constituting a surface of the hardened liquid material.

16. The method set forth in claim 15 wherein said step of allowing comprises the steps of pressing said wax against said mouth surface so that said hardenable liquid material is in contact with said mouth surface, and removing, from said mouth surface upon hardening of said liquid material, said wax together with the hardened liquid material.

17. The method set forth in claim 16 wherein said step of employing includes the steps of (a) placing said web onto the hardened liquid material upon removal of said wax and the hardened liquid material from said mouth surface, and (b) pressing said web against said mouth surface via the hardened liquid material.

18. The method set forth in claim 16 wherein said step of employing includes the steps of (a) placing said web onto said mouth surface upon removal of said wax and the hardened liquid material from said mouth surface, and (b) pressing said web against said mouth surface via the hardened liquid material.

19. A method for generating an electronic representation of a given surface of a tooth in a patient's mouth, comprising the steps of:

provid an applicator member carrying a predetermined pattern of reference marks having predetermined dimensions and intermark spacings, said applicator member taking the form of a deformable flexible web having an adhesive layer on at least one side and a concave surface;

applying a hardenable plastic filler material to said concave surface;

positioning said web with said hardenable plastic filler material on a prepared surface of the tooth;

shaping said hardenable plastic filler material and said web to assume a desired tooth restoration surface;

allowing said hardenable plastic filler material to harden;

upon hardening of said plastic filler material, optically scanning said tooth and said tooth restoration surface to generate a video signal encoding information as to the given surface of the tooth and said reference marks; and using reference information provided by said reference marks and contained in said video signal to produce the electronic representation of the given surface.

* * * * *